United States Patent [19]

Heppenstall et al.

[11] Patent Number: 4,620,543
[45] Date of Patent: Nov. 4, 1986

[54] ENHANCED FRACTURE HEALING AND MUSCLE EXERCISE THROUGH DEFINED CYCLES OF ELECTRIC STIMULATION

[75] Inventors: R. Bruce Heppenstall, Wynnewood; David W. Shenton, Philadelphia, both of Pa.

[73] Assignee: Richards Medical Company, Memphis, Tenn.

[21] Appl. No.: 620,870

[22] Filed: Jun. 15, 1984

[51] Int. Cl.⁴ .............................................. A61N 1/32
[52] U.S. Cl. ............................. 128/419 F; 128/423 R
[58] Field of Search ............. 128/421, 422, 423, 419 F

[56] References Cited

U.S. PATENT DOCUMENTS

| | | | |
|---|---|---|---|
| 2,434,497 | 1/1948 | Kearsley | 128/421 |
| 3,185,939 | 5/1965 | Moss et al. | 128/422 |
| 3,783,880 | 1/1974 | Kraus | 128/82.1 |
| 3,918,440 | 11/1975 | Kraus | 128/82.1 |
| 4,105,017 | 8/1978 | Ryaby et al. | 128/1.5 |
| 4,147,171 | 4/1979 | Greene et al. | 128/422 |
| 4,177,819 | 12/1979 | Kofsky et al. | 128/422 |
| 4,266,532 | 5/1981 | Ryaby et al. | 128/1.5 |
| 4,266,533 | 5/1981 | Ryaby et al. | 128/1.5 |
| 4,315,503 | 2/1982 | Ryaby et al. | 128/1.5 |
| 4,326,534 | 4/1982 | Axelgaard et al. | 128/421 |
| 4,342,317 | 8/1982 | Axelgaard | 128/419 R |
| 4,372,319 | 2/1983 | Ichinomiya et al. | 128/421 |
| 4,412,540 | 11/1983 | Bentall | 128/422 |
| 4,467,808 | 8/1984 | Brighton et al. | 128/419 F |
| 4,467,809 | 8/1984 | Brighton | 128/419 R |
| 4,492,233 | 1/1985 | Petrofsky et al. | 128/421 |
| 4,510,925 | 4/1985 | Constantinescu | 128/1.3 |

FOREIGN PATENT DOCUMENTS 840420 6/1952 Fed. Rep. of Germany ...... 128/421

OTHER PUBLICATIONS

"Noninvasive, Nondestructive Approaches to Cell Bioenergetics", Proc. Natl. Acad. Sci. USA, vol. 77, No. 12, pp. 7430–7434, Dec. 1980.

Primary Examiner—William E. Kamm
Attorney, Agent, or Firm—Pravel, Gambrell, Hewitt & Kimball

[57] ABSTRACT

Method for applying electro-muscular stimulation within a specific range of on/off cycle wherein the length of the on/off cycle is related to the level of phosphocreatine within the muscle. The on cycle is for a period of from one to three seconds followed by an off cycle of from 50 to 110 seconds in order to reduce the level of phosphocreatine in the muscle during the on period and allow subsequent recovery during the off period. The cycle is repeated for any desired period.

6 Claims, 2 Drawing Figures

FIG.

ENHANCED FRACTURE HEALING AND MUSCLE EXERCISE THROUGH DEFINED CYCLES OF ELECTRIC STIMULATION

TECHNICAL FIELD OF THE INVENTION

This invention relates to the treatment of bone and muscle irregularities through electro-muscular stimulation known as "EMS".

BACKGROUND OF THE INVENTION

In recent years, electrical stimulation has been used extensively in clinical rehabilitation settings where patients demonstrate difficulties with voluntary movement. Application of an electrical field transcutaneously to an innervated muscle produces excitation of a motor unit (i.e., nerves and muscle fibers innervated by that nerve). This ability to excite immobilized muscles has numerous reported benefits including the reduction of atrophy, reduction of post-op rehabilitation time, correction of contractures, facilitation of voluntary motor function, maintaining ranges of motion, avoiding adhesions, increasing muscle bulk, reducing swelling, relieving pain, and improving fatigue resistance. While such devices have been found beneficial, the results have been somewhat inconsistent.

Numerous devices and methods of applying EMS are readily available. Generally these muscles stimulators use comparatively long "on" periods of stimulation and short "off" periods of non-stimulation which overstimulate the muscles. Known commercially available stimulators are typically only used for relatively short periods of between 15 minutes and a few hours each day without patient discomfort, muscle fatigue, and muscle atrophy. Such stimulators have been built on the theory that in order for muscles to be built up, the muscles must first be exhaustively stimulated. A multitude of diverse and disassociated treatment regimens using this theory have produced stimulators with widely varied stimulation parameters. The relevant parameters are current or voltage amplitude, pulse duration, frequency of the pulse, on versus off duty cycles and wave forms. Optimum application of these parameters has not previously been discovered.

Duty cycles in most stimulators are capable of variation by the operator or patient based on personal preference rather than knowledge as to the optimum stimulation parameters necessary to enhance fracture healing and muscle maintenance. It has been found that commercially available stimulators have on periods of stimulation in duty cycles which are typically too long or off periods in duty cycles which are too short. Such stimulators consequently have produced mediocre and mixed results in clinical application.

Little basic research relating bio-energetic demand to voluntary or EMS induced muscle exercise has been conducted. Research has been limited by the time-consuming and destructive means of monitoring cellular metabolic demand through muscle biopsies. However, Phosphorus Nuclear Magnetic Resonance (31/P-NMR) spectroscopy has recently been used for non-invasive monitoring of several important metabolic parameters of muscle exercise including high energy phosphates (ATP) and phosphocreatine (PCR), inorganic phosphate ($P_i$), and sugar phosphates. Britton Chance has reported that exercise causes breakdown of PCR and concomitant increases in $P_i$ resulting in a decrease of PCR/$P_i$ monitored by 31/P-NMR analysis. (See, B. Chance, Non-invasive, Non-destructive Approaches to Cell Bio-Energetics, *Proc. Natl. Acad. Sci. U.S.A.*, 77:12, 7430-34, 1980.)

Prior effects to utilize electrical stimulation to treat muscle and bone irregularities include a family of patents by Ryaby et al. U.S. Pat. No. 4,105,017 is directed to a method of inducing patterns of electrical charge in a magnetic field. U.S. Pat. No. 4,315,503 is directed to a device for producing particular patterns of electrical voltage and current. U.S. Pat. Nos. 4,266,532 and 4,266,533 are directed to body treatment devices for applying electrical charge. These patents disclose the use of sequential electric charges in particular wave forms designed to control the behavior of non-excitable cells involved in tissue growth, repair and maintenance. The method utilizes a pattern of electrical charge from a stimulator to create a magnetic field with duty cycles in the range of 1% to 30% combined with on periods of stimulation as high as 5 milliseconds.

Axelgaard, et al. discloses in U.S. Pat. No. 4,326,534 and U.S. Pat. No. 4,342,317 method and apparatus for applying electrical muscle stimulation for the treatment of scoliosis and other spinal deformities. The method utilizes a pattern of electrical charges alternately applied to muscle groups on opposite sides of the deformity. The pattern of electrical charges represents a square wave with a preferred duty cycle of 25% and variable on/off periods between 4 and 40 seconds.

Kraus also provides a method and apparatus, U.S. Pat. Nos. 3,783,880 and 3,918,440, respectively, intended to aid the formation of bone forming material by electrical stimulation. The method utilizes a charge which is applied continuously at a specified current density and frequency.

The methods and associated charge generators disclosed by these patents either inadequately stimulate muscles by providing on periods of charge of insufficient duration or do not allow stimulated muscles sufficient time to relax during the off period after each electric charge. The prior art does not teach or provide sufficient stimulation and consequent substantial relaxation of muscles to prevent muscle atrophy and enhance fracture healing.

A number of muscle stimulators are commercially available which attempt to exercise muscles to prevent atrophy and encourage bone formation. A representative device is marketed under the trade name Zimmer "R" by Zimmer U.S.A., of Warsaw, Ind. U.S.A. The Zimmer stimulator provides duty cycles which can be varied between 10% and 90%; on periods of stimulation which vary between 3.5 and 34 seconds; and off periods of stimulation which vary between 10 and 225 seconds. This stimulator suffers from the same shortcomings of prior patents in that known methods of its use do not contemplate or teach optimum periods of muscle stimulation and rest required by the method of the present invention.

SUMMARY OF THE INVENTION

It is an object of this invention to provide an electro-muscular stimulation method utilizing a relatively short on cycle in combination with a relatively long off cycle to provide for enhanced fracture healing and muscle stimulation. It is a further object of this invention to provide a method of application of electro-muscular stimulation which can be applied substantially continuously day after day over a trauma period such as over the period of healing of a broken bone.

These objects and other objects of this invention are accomplished by the method of this invention for enhancing fracture healing and muscle vitality through providing on/off duty cycles for electrical stimulation including providing a therapeutic electric charge to a muscle group for on period of sufficient duration to substantially deplete the energy of the muscle group and providing an off period of sufficient duration to allow the muscle group to regain a substantial amount of energy depleted during stimulation. The method of this invention further includes the step of providing an on period for application of electro-muscular stimulation of sufficient length to substantially decrease the phosphocreatine in the muscle group. Specifically, the method of this invention provides an electro-muscular stimulation duty cycle including an on duty cycle of equal to or less than 2 seconds in combination with an off duty cycle of approximately 80 seconds.

These features and other features of this invention will be described in greater detail hereinafter. It should be understood that the summary of the invention does not necessarily disclose all features which are believed to be patentable and that the claims as set forth herein will set forth the features believed to be patentable.

DESCRIPTION OF THE PREFERRED EMBODIMENT

Figure 1:
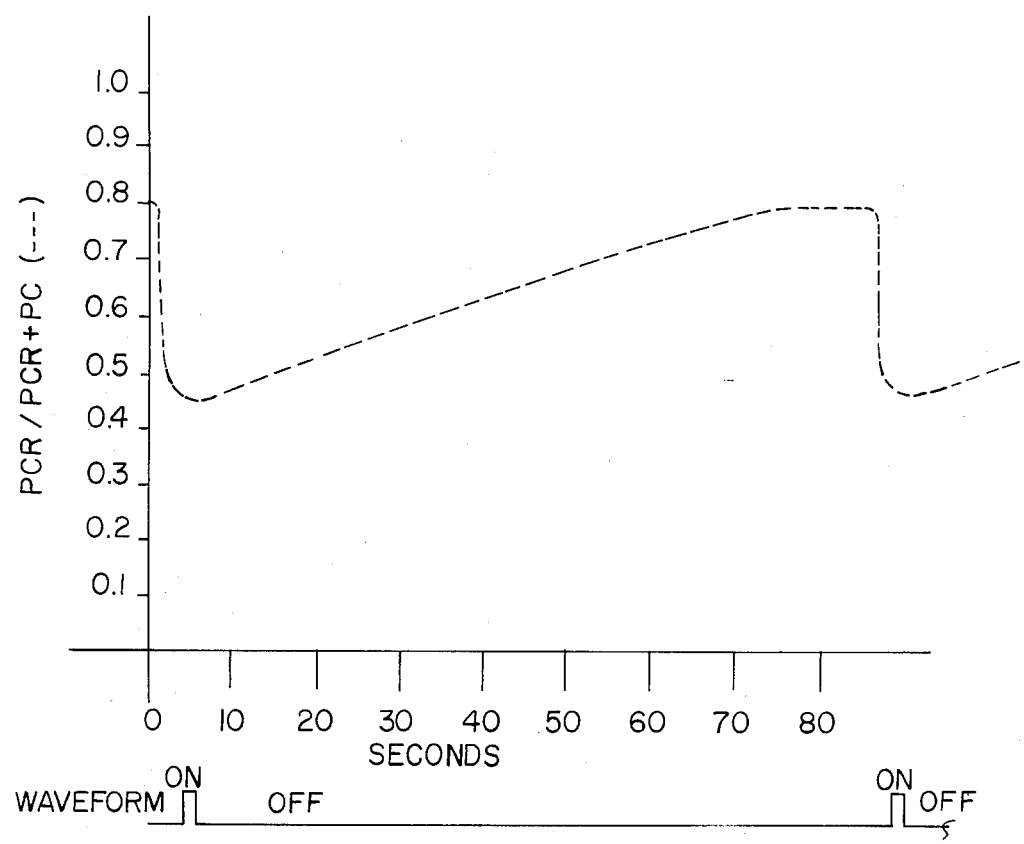
FIG. 1 is a graph showing the relationship between on and off duty cycles and the phosphocreatine/phosphocreatine plus inorganic phosphate ratio.
Figure 2:
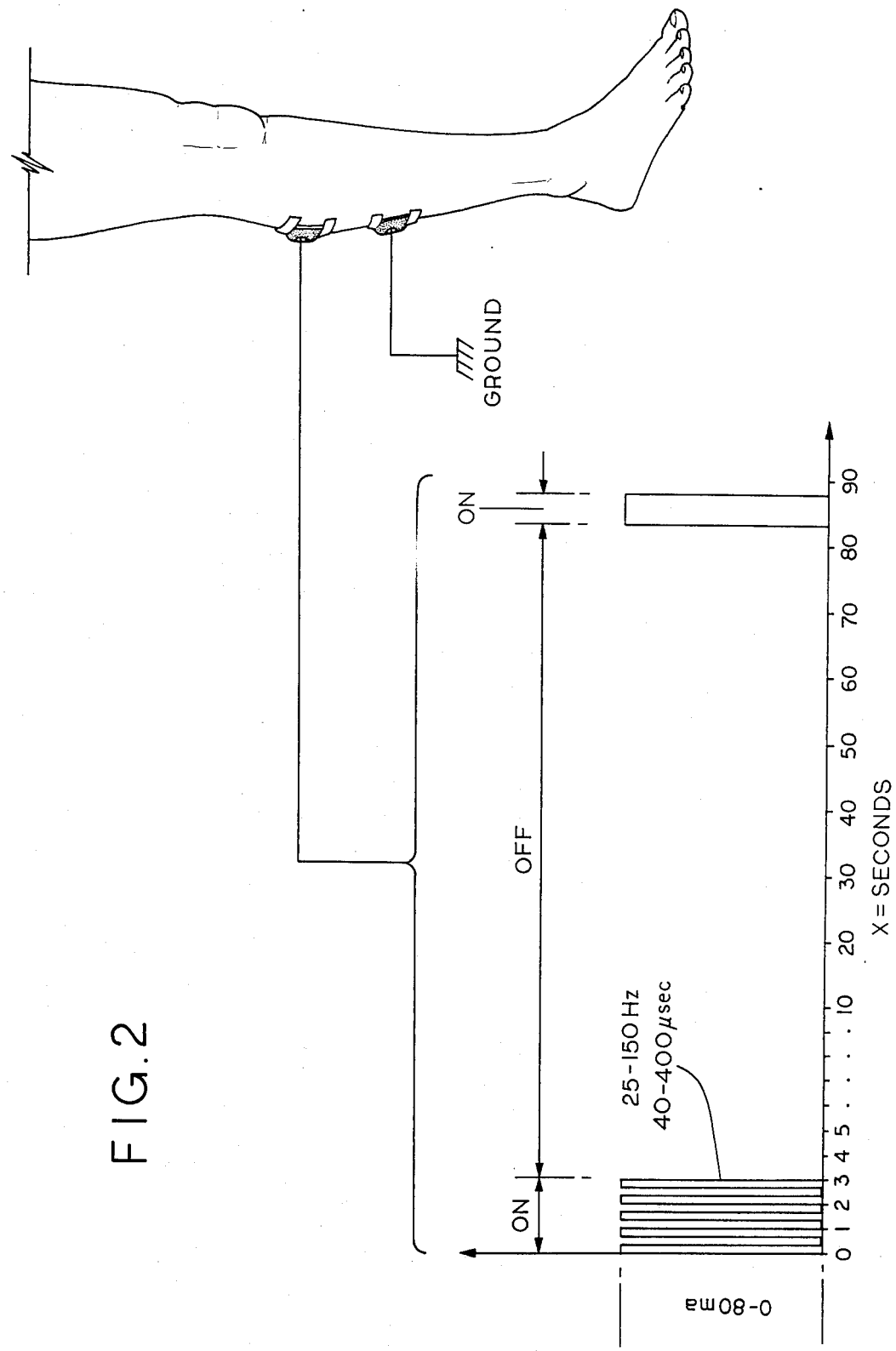
FIG. 2 is a schematic drawing showing the range of on and off duty cycles of electrical stimulation and schematically illustrating the application of such electrical stimulation to a body member.

While research and practical application of electro-muscular stimulation is well-known, optimization of maintenance of muscle vitality and enhancement of bone healing through muscle stimulation has heretofore been unknown. Indeed, it has been learned that certain amplitudes and on/off duty cycles may even be detrimental to the healing process. It has been discovered that the electro-muscular stimulation should be tetanic, that is, that the amplitude, frequency and duration of electro-muscular stimulation should be sufficiently great that the muscle is excited sufficiently to induce prolonged contraction.

It has further been discovered that the off cycle duration is important to the healing process. It has been discovered that relatively short off cycles such as 8-15 seconds may even detrimental to muscle maintenance. It has further been discovered that certain parameters relating to chemical balances within muscles may be effective benchmarks in the determination of effective and optimal muscle stimulation cycles. It has been determined that short, intense bouts of tetanic electro-muscular stimulation result in a metabolic demand which is similar to the intensive voluntary resistive exercise which leads to proper muscle maintenance and healing and which is of course unavailable to trauma patients having broken bones or the inability to exercise muscles.

It is believed that a measurable and important parameter of muscle contraction and relaxation is the level of phosphocreatine within the muscle. Utilizing a more recently available research method known as nuclear magnetic resonance (31/P-NMR) spectroscopy, the level of phosphocreatine and inorganic phosphates within the muscle has been studied during on and off duty cycles. It has been determined that the most beneficial on and off duty cycles can be determined from a study of the depletion and recovery of phosphocreatine within the stimulated muscle.

It has been determined that it is necessary to apply sufficiently intensive tetanic electro-muscular stimulation to cause significant depletion in the level of phosphocreatine in the stimulated muscle. It has further been determined important to allow the level of phosphocreatine within the muscle to be replaced during a rest period prior to application of sequential stimuli. It has been determined that the on-time of electro-muscular tetanic stimulation should be sufficient to allow for a substantial phosphocreatine depletion while avoiding a lactic acid build up within the muscle.

The following range of parameters are considered to provide beneficial results:

| Parameter | Range | Optimum Setting |
|---|---|---|
| Current (Galvanic) | 0-80 milliamps | Related to Muscle Mass |
| Pulse Duration | 40-400 microseconds | 300 microseconds |
| Frequency (Tetanic) | 25-150 Hz | 70 Hz |
| On Duty Cycle | 1-3 seconds | 2 seconds |
| Off Duty Cycle | 50-110 seconds | 80 seconds |

It has further been determined that the optimum on-duty cycle should be approximately 2 seconds and the optimum off-duty cycle should be in the range of 60-80 seconds and preferably 80 seconds. It should be understood that while these are considered optimum levels that specific application to specific muscles of various locations and sizes may require some adjustment of the optimum range which will be within the scope of this invention.

Referring to the Figure, the X-axis is a time line in seconds and the Y-axis is the ratio of phosphocreatine to the sum of phosphocreatine plus inorganic phosphorous (PCR/PCR+Pi). During the optimal on period, the PCR/PCR+Pi ratio is reduced to below 0.5 and the off period is of sufficient length to allow the ratio to approach 1.0 to allow full recovery of the muscle before applying sufficient tetanic excitation to again substantially reduce the PCR/PCR+Pi ratio. It should be understood that the graph does not represent actual historical application only, rather, the graph is a composite based on historical information and intuitive study relating to this invention.

The electro-muscular stimulation (EMS) apparatus is not illustrated since such devices are known in the art. Typically, such apparatus includes a wave form generator, an oscillator, galvanic power supply, current regulator and feedback monitor which can provide a square, monophasic, galvanic wave form of the above listed frequency. Additionally, means are provided for adjusting the amplitude of the induced pulses over the period of the on cycle for the benefit of patient comfort. As previously mentioned, such apparatus has not been used in the combination of parameters taught herein. Various devices are commercially available which have the necessary components to provide the electrical stimulation within the method of this invention. For example, the "710 NMS Neuromuscular Stimulator" manufactured by EMPI of 261 South Commerce Circle, Fridley, Minn. is a device having the necessary electrical components to provide output amplitude, pulse width, pulse rate and charge pulse in a combination of timed on and off duty cycles. However, neither this device nor any of the other prior art devices have been used in the combination of parameters and on and off duty cycles disclosed in the method of this invention. Though the EMPI 710 NMS Neuromuscular Stimulation is not in its commercial form capable to practicing the method of this invention, it would be a matter of obvious design skill to modify such device given the teaching of this invention.

Utilizing the apparatus of this invention and its method, it is believed that electro-muscular stimulation can be applied to a patient with a high level of comfort. It is believed that the application of this method which allows for the muscle to return to a substantially rested condition between the short, high intensity tetanic electro-stimulations, provides for a substantially continuous application of electro-muscular stimulation over the course of a day. For example, it is contemplated that the method and apparatus of this invention can be applied to a patient for a period such as 16 hours a day. The overall beneficial healing provided on a daily basis can therefore be built upon over a substantially continuous period of days to thereby decrease effectively the healing time and otherwise provide for a beneficial maintenance of muscle vitality.

In applying the method of this invention, the electrodes of the apparatus are placed upon motor points of the muscle, which need to be determined on a case-by-case, location-by-location basis as is well-known in the art. It is contemplated that an oscilloscope (not shown) may also be used to monitor voltage and amperage and that a "soft" type of turn-on may be utilized to add to patient comfort.

While the method and apparatus of this invention has been discussed most specifically in terms of the enhancement of fracture healing and the maintenance of muscle surrounding a bone fracture, it should be understand that any type of trauma or chronic muscle disease or condition may be benefited by the method of this invention. It is believed that the method and apparatus of this invention contributes to the enhancement of fracture healing including a stimulation of bone growth, though the stimulation of bone growth has not been verified to date. Additionally, positive muscle build up may be provided for the field of sports medicine and recovery from sports related injuries.

The foregoing disclosure and description of the invention are illustrative and explanatory thereof, and various changes in the size, shape and materials, as well as in the details of the illustrated construction may be made without departing from the spirit of the invention.

We claim:

1. A method of enhancing fracture healing and muscle vitality through on/off duty cycles of electric stimulation comprising:
   providing a therapeutic electric charge to a muscle group for an on period of electrical stimulation by applying said electrical stimulation in galvanic power of:
   a. pulses at 25 to 150 Hz;
   b. having a pulse width of 40 to 400 microseconds; and
   c. having an amplitude of current between 0 and 80 milliamps
   for a period of 1–3 seconds to substantially deplete the energy of the muscle group;
   providing an off period of at least 50 seconds and not more than 110 seconds duration to allow the muscle group to regain a substantial amount of energy depleted during stimulation; and
   sequentially applying said on and off duty cycles to such muscle group.

2. The method of claim 1, including:
   providing said on period for said 1–3 seconds to reduce the phosphocreatine/phosphocreatine plus inorganic phosphorate ratio to below approximately 0.8 during the on period of muscle stimulation.

3. The method of claim 1 in which:
   allowing the phosphocreatine/phosphocreatine plus inorganic phosphorus ratio to return to at least 0.8 during the off period of said 50 seconds to 110 seconds of relaxation of the muscle group.

4. The method set forth in claim 1, including:
   providing said off period for at least 60 seconds and not more than 80 seconds.

5. The method of claim 1 in which:
   providing said electric charge in a substantially rectangular wave form during said on period.

6. The method of electrical stimulation recited in claim 1 in which:
   a. the on duty cycle is two seconds; and
   b. the off duty cycle is 80 seconds.

* * * * *